United States Patent
Gultekin

(10) Patent No.: US 7,246,939 B1
(45) Date of Patent: Jul. 24, 2007

(54) MEASUREMENT OF THERMAL DIFFUSIVITY, THERMAL CONDUCTIVITY, SPECIFIC HEAT, SPECIFIC ABSORPTION RATE, THERMAL POWER, HEAT TRANSFER COEFFICIENT, HEAT OF REACTION AND MEMBRANE PERMEABILITY BY NUCLEAR MAGNETIC RESONANCE

(76) Inventor: David H. Gultekin, 125 Esperanza Ave., Apt. 5, Sierra Madre, CA (US) 91024

( * ) Notice: Subject to any disclaimer, the term of this patent is extended or adjusted under 35 U.S.C. 154(b) by 177 days.

(21) Appl. No.: 10/971,910

(22) Filed: Oct. 23, 2004

Related U.S. Application Data

(60) Provisional application No. 60/513,702, filed on Oct. 23, 2003.

(51) Int. Cl.
  G01N 25/02 (2006.01)
  G01N 25/20 (2006.01)
  G01V 3/14 (2006.01)
  A61B 5/00 (2006.01)

(52) U.S. Cl. .................. 374/44; 374/117; 600/412; 324/307

(58) Field of Classification Search .............. 374/44
  See application file for complete search history.

(56) References Cited

U.S. PATENT DOCUMENTS

| | | | |
|---|---|---|---|
| 4,115,730 A | 9/1978 | Mansfield | |
| 4,145,922 A | 3/1979 | Estrada, Jr. et al. | |
| 4,283,935 A | 8/1981 | Eguchi et al. | |
| 4,522,512 A | 6/1985 | Atkins | |
| 4,558,279 A * | 12/1985 | Ackerman et al. | 324/315 |
| 4,568,198 A | 2/1986 | Szabó et al. | |
| 4,808,928 A | 2/1989 | Frahms et al. | |
| 4,914,608 A * | 4/1990 | LeBihan et al. | 702/131 |
| 4,944,035 A | 7/1990 | Aagardl et al. | |
| 5,162,736 A | 11/1992 | Mansfield et al. | |
| 5,168,228 A | 12/1992 | Mansfield et al. | |
| 5,207,222 A * | 5/1993 | Koizumi et al. | 600/412 |
| 5,263,482 A * | 11/1993 | Leunbach | 600/412 |
| 5,289,124 A * | 2/1994 | Jerosch-Herold et al. | 324/303 |
| 5,327,884 A * | 7/1994 | Hardy et al. | 600/411 |
| 5,343,150 A * | 8/1994 | Nakahata et al. | 324/316 |
| 5,368,031 A * | 11/1994 | Cline et al. | 600/411 |
| 5,713,665 A | 2/1998 | Kato et al. | |
| 5,988,875 A | 11/1999 | Gershfeld et al. | |
| 6,280,384 B1 * | 8/2001 | Loeffler | 600/412 |
| 6,669,688 B2 | 12/2003 | Svaasand et al. | |
| 6,676,287 B1 | 1/2004 | Mathis et al. | |
| 6,766,071 B2 | 7/2004 | Whateley | |
| 6,823,216 B1 * | 11/2004 | Salomir et al. | 607/101 |
| 6,825,667 B1 * | 11/2004 | Tsuda | 324/320 |

(Continued)

FOREIGN PATENT DOCUMENTS

JP 09262222 A * 10/1997

OTHER PUBLICATIONS

Measurement of thermal diffusivity by magnetic resonance imaging. Article by Gultekin et al. 2006.*

(Continued)

*Primary Examiner*—Gail Verbitsky

(57) ABSTRACT

This invention utilizes the nuclear magnetic resonance imaging and spectroscopy to experimentally measure thermal diffusivity, thermal conductivity, specific heat, specific absorption rate, thermal power, heat transfer coefficient, heat of reaction and the membrane permeability in substances and systems.

22 Claims, 8 Drawing Sheets

U.S. PATENT DOCUMENTS

| | | | |
|---|---|---|---|
| 7,136,516 B2 * | 11/2006 | Alyassin | 382/128 |
| 2002/0058869 A1 * | 5/2002 | Axelsson et al. | 600/423 |
| 2003/0039299 A1 * | 2/2003 | Horovitz et al. | 374/141 |
| 2004/0004478 A1 * | 1/2004 | Hofmann et al. | 324/321 |
| 2004/0176680 A1 * | 9/2004 | Moonen et al. | 600/411 |
| 2005/0090732 A1 * | 4/2005 | Ivkov et al. | 600/411 |
| 2005/0122102 A1 * | 6/2005 | Reddy et al. | 324/307 |
| 2006/0038563 A1 * | 2/2006 | Chisholm et al. | 324/309 |
| 2006/0064002 A1 * | 3/2006 | Grist et al. | 600/410 |
| 2006/0192559 A1 * | 8/2006 | Ardenkjaer-Larsen et al. | 324/321 |
| 2006/0239328 A1 * | 10/2006 | Sumi | 374/43 |

OTHER PUBLICATIONS

Hai-Ling Margaret Cheng, Donald B. Plewes. Tissue Thermal Conductivity by Magnetic Resonance Thermometry and Focused Ultrasound Heating. Journal of Magnetic Resonance Imaging, 16:598-609 (2002).

\* cited by examiner

MEASUREMENT OF THERMAL DIFFUSIVITY, THERMAL CONDUCTIVITY, SPECIFIC HEAT, SPECIFIC ABSORPTION RATE, THERMAL POWER, HEAT TRANSFER COEFFICIENT, HEAT OF REACTION AND MEMBRANE PERMEABILITY BY NUCLEAR MAGNETIC RESONANCE

CROSS-REFERENCE TO RELATED APPLICATIONS

This application claims priority benefit of provisional U.S. application Ser. No. 60/513,702, filed on Oct. 23, 2003.

FEDERALLY SPONSORED RESEARCH

Not Applicable

SEQUENCE LISTING OR PROGRAM

Not Applicable

FIELD OF THE INVENTION

This invention involves the experimental measurements of thermal diffusivity, thermal conductivity, specific heat, specific absorption rate, thermal power, heat transfer coefficient, heat of reaction and the membrane permeability in substances by nuclear magnetic resonance.

BACKGROUND OF THE INVENTION

The physical, thermophysical and transport properties of the substances are important in physics, chemistry, biochemistry, medicine, polymer science, food science, materials science, thermal science and engineering. This invention involves the experimental measurements of thermal diffusivity, thermal conductivity, specific heat, specific absorption rate, thermal power, heat transfer coefficient, heat of reaction and the membrane permeability in substances by nuclear magnetic resonance (NMR). This invention is applicable to a wide range of substances and objects and the advantages of the present invention are:

The NMR method is a non-contact and non-invasive method. Measurement of thermal diffusivity in substances is important to a number of applications ranging from medicine to chemistry and engineering. The applications of this method in medicine are in thermal treatment of tissues (normal or abnormal) and tumors (benign or malignant) in oncology (human or animal patients). The method can be used in monitoring the diffusion of thermal energy during the treatment of tumors. The method is also applicable to materials science, chemistry and engineering. The method allows for measurement of thermal diffusivity in very small quantities of substances.

The measurement of thermal conductivity is important in a number of applications in physics, chemistry, biochemistry, medicine, materials science and engineering. The non-contact and non-invasive measurement of thermal conductivity can be used during the thermal treatment of tissues and tumors in oncology. The method also finds a number of applications in materials science, chemistry and engineering. The method allows for the measurement of thermal conductivity in very small quantities of substances.

The measurement of specific heat and specific absorption rate is important to materials science, chemistry, physics, medicine and thermal science. The measurement of specific heat allows for the measurement of specific absorption rate in substances subjected to electromagnetic radiation. This method is applicable to characterization of tissue absorption rates in radiology and oncology. The method has a number of applications in chemistry, biochemistry, materials science and engineering. The method also provides means for the measurement of specific heat and specific absorption rate in small quantities of the substances.

The heat transfer coefficient is important in a number of applications ranging from medicine to food science and engineering. The non-invasive and non-contact NMR method of measuring heat transfer coefficient can improve the thermal treatment of tissues and tumors in oncology. The method also finds applications in food science where food is frequently subjected to thermal treatment in aseptic processing. The other applications are in measurement and characterization of biological and thermal systems.

The heat of reaction is important in a number of applications in chemistry, biology, biochemistry, medicine, thermodynamics and materials science. NMR provides a non-invasive and a non-contact method to measure the changes in thermal energy in substances. The NMR calorimeter method can be used in measurement of heat of reaction in chemistry, biochemistry and biomedical applications. The method can also be used to measure the thermal power in thermal science, medical and biomedical application.

The measurement of membrane permeability is important to research in various disciplines. The mechanism of water and ion transport through membranes can be studied and quantitative measurements characterizing the membrane systems can be made using nuclear magnetic resonance methods. The differences between the membranes can be seen using nuclear magnetic resonance imaging and the apparent membrane permeability can be measured experimentally in membrane and solution systems.

SUMMARY OF THE INVENTION

In accordance with the present invention a heat source is applied to a substance and the resultant transport of thermal energy in the substance is monitored in space and time using the nuclear magnetic resonance parameters of the substance. The thermal source and the substance under examination are placed in a nuclear magnetic resonance system. The heat source can be continuous or pulsed and its geometry depends on the choice of coordinate system under the measurement. By monitoring the spatial and temporal variation of NMR parameters with thermal energy the thermal diffusivity, thermal conductivity and specific heat in substances are measured experimentally. The specific heat is then used to measure the specific absorption rate of the substance subjected to electromagnetic radiation. When the substance with known specific heat is subjected to a thermal convection or radiation then the thermal power of the thermal system is measured experimentally. Subjecting a substance to convective heat transfer and measuring the temporal variation of a dimensionless nuclear magnetic resonance parameter results in measurement of heat transfer coefficient of the substance and fluid system as a function of fluid flow rate. Reacting chemicals in an impermeable membrane cell imbedded in a substance of known specific heat and by measuring the temperature rate in the substance, the heat of reaction for the chemicals can be measured experimentally. Separating a solvent from a solution containing a salute by a permeable or semi permeable membrane and by measuring a nuclear magnetic resonance parameter in cells over time the apparent membrane permeability can be measured experimentally by nuclear magnetic resonance.

DETAILED DESCRIPTION OF THE INVENTION

Figure 1:
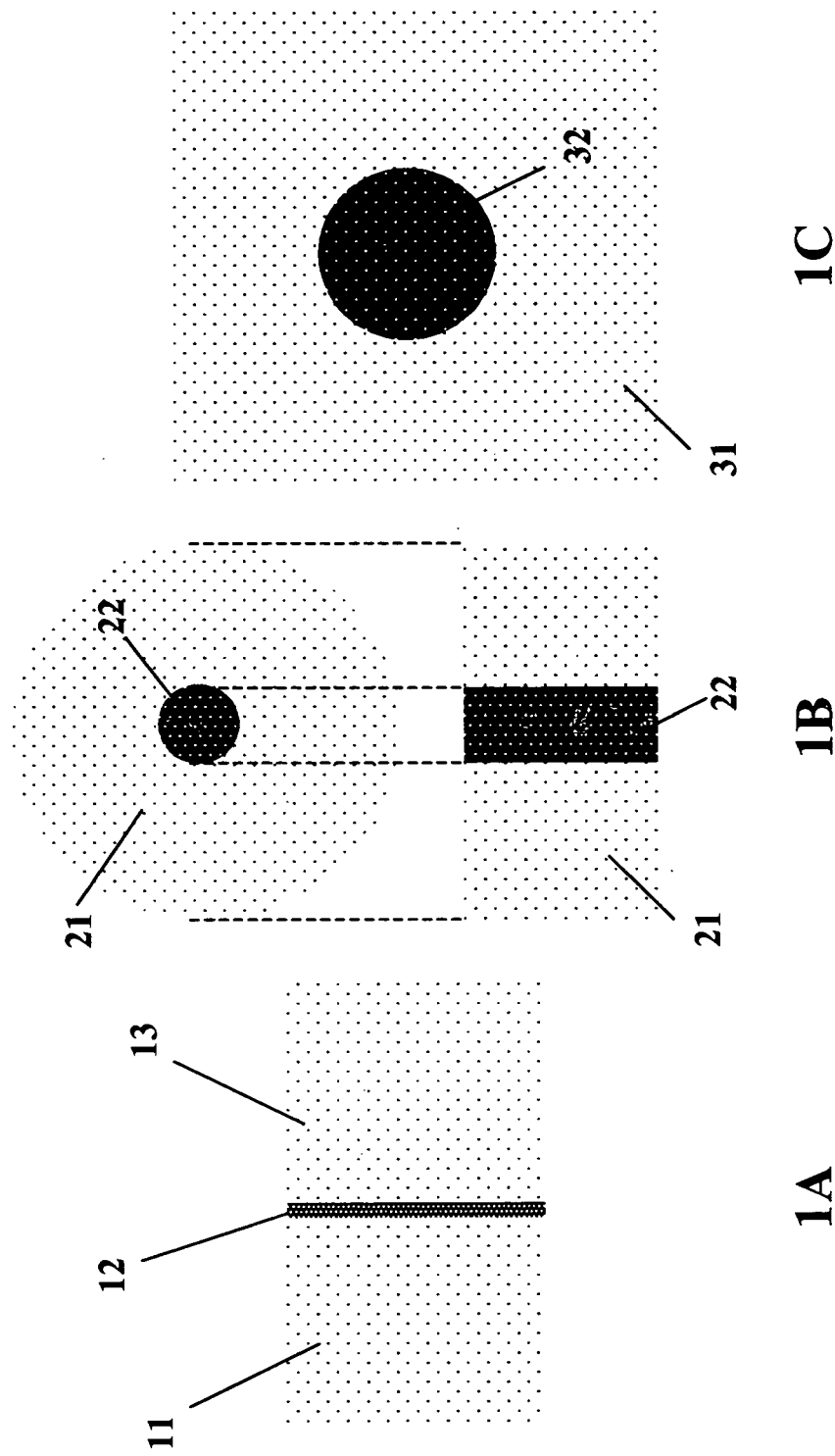
FIG. 1A to 1C is a simplified experimental setup for measuring thermal diffusivity, thermal conductivity, specific heat and specific absorption rate, thermal power, heat transfer coefficient, heat of reaction and membrane permeability by nuclear magnetic resonance.

This novel approach involves application of a thermal source to a substance and the measurement of spatial and temporal variation of one or more of several nuclear magnetic resonance parameters (nuclear magnetic resonance frequency ω, nuclear spin phase shift φ, nuclear magnetization $M(t_e,T)$, equilibrium nuclear magnetization $M(0,T)$, spin-lattice relaxation time $T_1(T)$, spin-lattice relaxation rate $R_1(T)$, spin—spin relaxation time $T_2(T)$, spin—spin relaxation rate $R_2(T)$, effective spin—spin relaxation time $T_2^*(T)$, effective spin—spin relaxation rate $R_2^*(T)$ or spin diffusion coefficient $D(T)$) in the substance. From this, several thermophysical properties and transport parameters of the substances and thermal systems are measured using the nuclear magnetic resonance [1]. The thermal diffusivity, thermal conductivity and specific heat are measured by applying a thermal pulse and a thermal flux (a laser) to the substance and measuring the variation of thermal energy in space and time through a nuclear magnetic resonance parameter. The specific absorption rate is measured by subjecting the substance to the electromagnetic radiation and measuring the rate of temperature. The specific absorption rate in substance is then calculated using the specific heat and the rate of temperature. The heat transfer coefficients of fluid and particle systems are measured through two nuclear magnetic resonance parameters in substances. The details of the measurements of these parameters by nuclear magnetic resonance methods are given below.

We consider the behavior of the thermally induced magnetic field at the nuclei of atoms, B, which we assume is proportional to the external field through the temperature dependent nuclear shielding, σ(T), as $$B = (1-\sigma(T))B_0 \quad (1)$$

In the absence of any temporal variation of the external magnetic field, the temporal variation of magnetic field experienced by nuclei (over time scales much larger than the times between intermolecular collisions or molecular rotations) will be due to the diffusion of thermal energy in the substance. In a uniform sample, therefore, B effectively moves in space and time with the transport of heat. The flux of B is related to the thermally induced magnetic field gradient through the thermal diffusivity, α, as $$j = -\alpha \nabla B \quad (2)$$

A laser pulse of heat applied at time t=0 at position $\epsilon=\epsilon_0$ is represented by a Dirac's delta function and provides the initial temperature conditions.

$$B(\epsilon,0) = H\delta(\epsilon-\epsilon_0) \quad (3)$$

where H is a magnetic field density in the plane perpendicular to ε. Using standard methods, the solution for B is then $$B(\varepsilon, t) = \frac{H}{2^n (\pi \alpha t)^{n/2}} e^{-\frac{(\varepsilon-\varepsilon_0)^2}{4\alpha t}} \quad (4)$$

where n is 1, 2 and 3 for Cartesian, cylindrical and spherical coordinate systems, respectively. After the application of a laser pulse at one location, the thermally induced field diffuses away but at any distance the value of this perturbation will maximize at a time that depends on the distance and the thermal diffusivity of the substance. The time corresponding to the maximum change can be obtained by setting the first temporal derivative of Eq. (4) equal to zero, $$\frac{\partial B(\varepsilon, t)}{\partial t} = 0 \quad (5)$$

from which $$(\epsilon-\epsilon_0)^2 = 2n\alpha t_m \quad (6)$$

relates the square distance to the time for a maximal change at any position, $t_m$, and the thermal diffusivity. A plot of $(\epsilon-\epsilon_0)^2$ versus $t_m$ yields a line with a slope of $2n\alpha$ from which the thermal diffusivity can be calculated for the substance.

The thermally induced magnetic field shift at the nuclei of atoms can be measured by measuring the nuclear spin phase shift through Larmor's equation $$\phi = -\gamma T_E B \quad (7)$$

where $\gamma$ is the gyromagnetic ratio and $T_E$ is the echo time. By measuring the phase of the relevant resonance at a fixed echo time we can compute the field perturbation and use this to track the heat flow.

The diffusion of thermal energy causes a spatial and temporal variation in the equilibrium nuclear magnetization via changes in Boltzman's distribution. We demonstrate below that the equilibrium nuclear magnetization and relaxation can be used to monitor the diffusion of thermal energy.

For measurements of the NMR signal we use a gradient echo sequence. If the flip angle is $\theta$ and the expression for the signal is given by $$M(T_E, T_R, T) = M(0, T)\sin\theta e^{-\frac{T_E}{T_2^*(T)}}\left(1 - e^{-\frac{T_R}{T_1(T)}}\right)\left(1 - e^{-\frac{T_R}{T_1(T)}}\cos\theta\right)^{-1} \quad (8)$$

where $M(0,T)$ is the equilibrium nuclear magnetization, $T^*_2(T)$ is the spin—spin relaxation time in the presence of field inhomogeneity, $T_R$ is the repetition time and $T_1(T)$ is the spin-lattice relaxation time.

Then, $$\frac{\partial \ln M(T_E, T_R, T)}{\partial T} = -\frac{1}{T} + \frac{T_E}{T_2^{*2}(T)}\frac{\partial T_2^*(T)}{\partial T} + \cot\theta\frac{\partial \theta}{\partial T} - \frac{T_R}{T_1^2(T)}\frac{\partial T_1(T)}{\partial T}\frac{E_1}{1 - E_1} - \left[\sin\theta\frac{\partial \theta}{\partial T} - \cos\theta\frac{T_R}{T_1^2(T)}\frac{\partial T_1(T)}{\partial T}\right]\frac{E_1}{1 - E_1\cos\theta} \quad (9)$$

where $$E_1 = e^{\frac{T_R}{T_1(T)}}.$$

The Eq. (9) indicates that the temperature dependence of the magnitude of NMR signal is a function of temperature, echo time, recovery time, spin—spin and spin-lattice relaxation times, and the manner in which relaxation times depend on temperature [2].

If we consider only the following cases $$T_R \gg T_1(T), \left|\frac{\partial \theta}{\partial T}\right| \ll 1 \quad (10)$$

then, Eq. (9) simplifies to $$\frac{\partial \ln M(T_E, T)}{\partial T} = -\frac{1}{T} + \frac{T_E}{T_2^{*2}(T)}\frac{\partial T_2^*(T)}{\partial T} \quad (11)$$

which can be used to monitor the diffusion of thermal energy in substances.

In Cartesian coordinate system, taking $z = \epsilon - \epsilon_0$, $$M(T_E, T, z, t) = \frac{M_s(T_E, T, 0, 0)}{2(\pi\alpha t)^{1/2}} e^{-\frac{z^2}{4\alpha t}} \quad (12)$$

where $M(T_E,T,z,t)$ is the temperature dependent nuclear magnetization and relaxation, $M_s(T_E,T,0,0)$ includes the thermally induced nuclear magnetization and relaxation produced by the pulse in the plane perpendicular to the direction of magnetic field and the direction of the propagation of thermal energy, t is the time of thermal diffusion.

Figure 2:
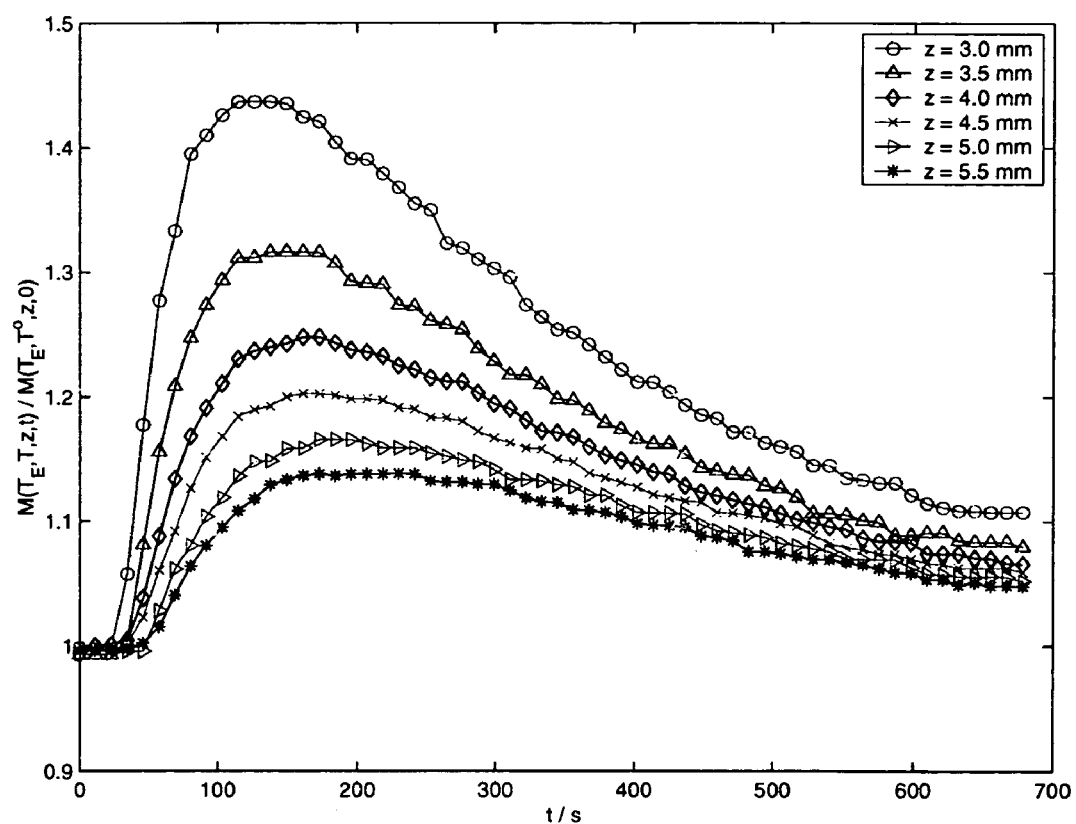
FIG. 2 is a plot of temporal and spatial variation of thermally induced nuclear magnetization and relaxation measured by a gradient echo sequence following a thermal pulse (a laser) for Glycerol. From this graph the thermal diffusivity of Glycerol is determined experimentally.

In the experimental configuration in FIG. 1A, with 11 being air, 12 being a light absorber and 13 being a sample of Glycerol, using a thermal pulse (a laser) the spatial and temporal variation of thermally induced nuclear magnetization as measured by a gradient echo sequence in a 2T Bruker system (Bruker, Germany) is shown in FIG. 2. The NMR parameters are $T_E$=11 ms, $T_R$=90 ms, BW=12.5 kHz, FOV=64 mm, m=128×128. The data are analyzed using the Matlab (Mathworks, U.S.A.). Using the data in FIG. 2, the thermal diffusivity of Glycerol is calculated as $0.94\cdot10^{-7}$ $m^2s^{-1}$ [3].

The thermal conductivity of a substance can be experimentally measured by applying a planar thermal flux and measuring the temperature gradient through Fourier's relation $$\kappa = -\dot{q}''/\nabla T \quad (13)$$

The temperature gradient can be measured by nuclear magnetic resonance phase shift imaging accurately. The shift in the phase of the spins is a function of the magnetic field strength ($B_0$) and echo time ($T_E$) for a given nucleus as $$\phi = \gamma \cdot (1 - \sigma(T))B_0 \cdot T_E \quad (14)$$

where $\sigma(T)$ is the nuclear shielding and it is temperature dependent.

The temperature dependence of nuclear spin phase shift as $$\left(\frac{\partial \phi}{\partial T}\right) = -\gamma B_0 T_E\left(\frac{\partial \sigma}{\partial T}\right) \quad (15)$$

in terms of nuclear thermal coefficients $$\phi_T = \frac{\partial \phi}{\partial T}, \quad \sigma_T = \frac{\partial \sigma}{\partial T} \quad (16)$$

gives the thermally induced phase shift $$\phi_T = -\gamma \cdot B_0 \cdot T_E \cdot \sigma_T \quad (17)$$

as a function of gyromagnetic ratio, magnetic field, echo time and the nuclear coefficient for nuclear shielding.

The nuclear thermal coefficients depend on the substances and can be determined experimentally by measuring the thermally induced phase shift as a function of temperature using the following relation.

$$d\phi = -\gamma B_0 \cdot T_E \cdot \sigma_T \cdot dT, \quad d\phi = \phi_T dT \quad (18)$$

The temperature gradient is then related to the phase shift gradient through the following relation $$\frac{dT}{dz} = \frac{1}{\phi_T}\frac{d\phi}{dz} \quad (19)$$

The rate of temperature relates to the rate of spin phase shift as $$\frac{dT}{dt} = \frac{1}{\phi_T}\frac{d\phi}{dt} \quad (20)$$

Substituting Eq. (19) into Eq. (13), the thermal conductivity becomes $$\kappa = -\dot{q}''\cdot(\gamma\cdot B_0\cdot T_E\cdot\sigma_T)\left(\frac{d\phi}{dz}\right)^{-1} \quad (21)$$

in terms of the heat flux and nuclear parameters.

Figure 3:
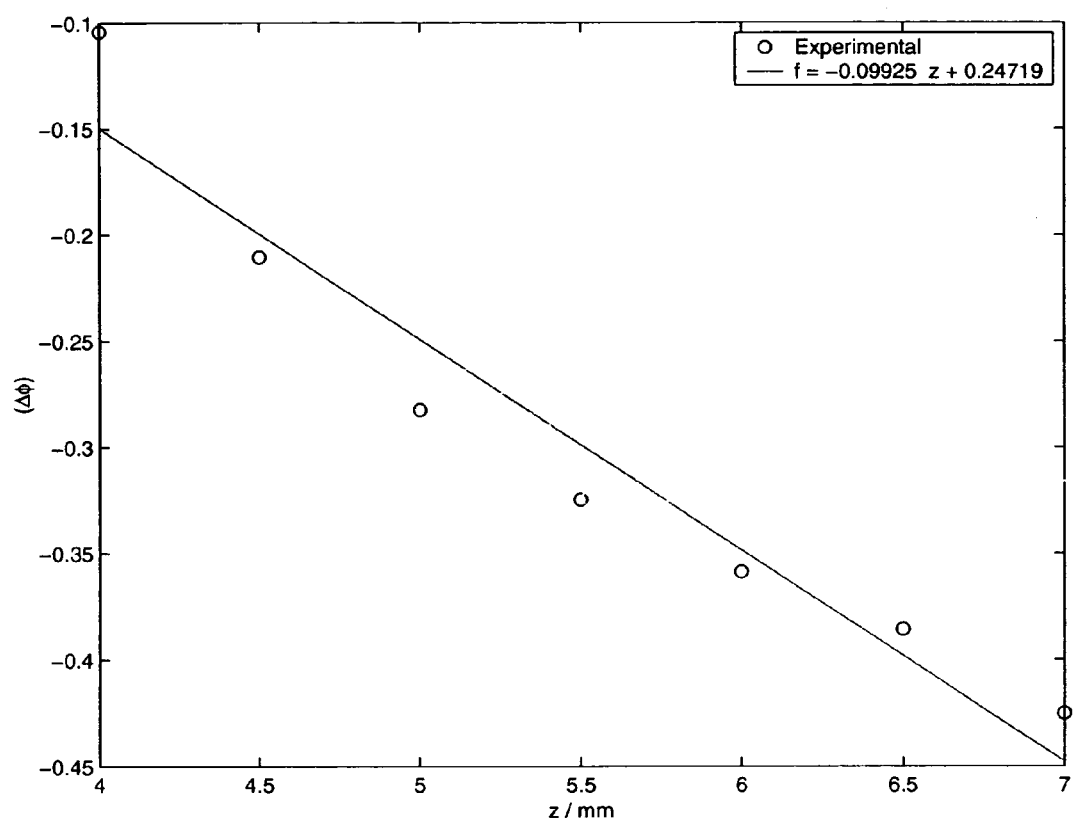
FIG. 3 is a plot of thermally induced nuclear spin phase shift in water measured by a gradient echo sequence versus space following the application of a thermal flux (a laser). From the data the thermal conductivity of water is determined experimentally.

As in FIG. 1B with 21 being a thermal insulator and 22 being a sample of water in a cylindrical cell (10 mm dia., 50 mm long) with its axis aligned with the direction of $B_0$ field is subjected to a thermal flux of $\dot{q}''=1146$ W/m² by a laser beam on an absorber at one end. The variation of nuclear spin phase shift as measured by a gradient echo sequence with distance from thermal source is shown in FIG. 3. Using the experimental NMR parameters of TE=11 ms, $\gamma=2.674\cdot10^8$ rads/s·T, $B_0=2$ T, $\sigma_T=-0.01$ ppm/K, $\phi_T=0.05885$ rads/K, and $d\phi/dz=-0.09925$ rads/mm from FIG. 3, the thermal conductivity is calculated as $\kappa=0.679$ W/m·K for a water sample [4].

The measurement of specific heat involves application of a constant power to the substance and measurement of the temperature rise with time. The thermal power can be written in terms of specific heat and temperature rate in a constant volume as $$\rho CV\frac{\partial T}{\partial t} = P(t) \quad (22)$$

Using a constant power and taking the specific heat as constant over a narrow temperature range (a range of few Kelvin), the temperature varies linearly with time as $$\frac{dT}{dt} = \frac{P}{\rho CV} \quad (23)$$

By relation in Eq. (20), and volume fraction of imaging slice $R_v$, the specific heat can be formulated as $$C = \frac{PR_v\phi_T}{\rho V}\left(\frac{d\phi}{dt}\right)^{-1} \quad (24)$$

as a function of power and rate of nuclear spin phase shift.

Figure 4:
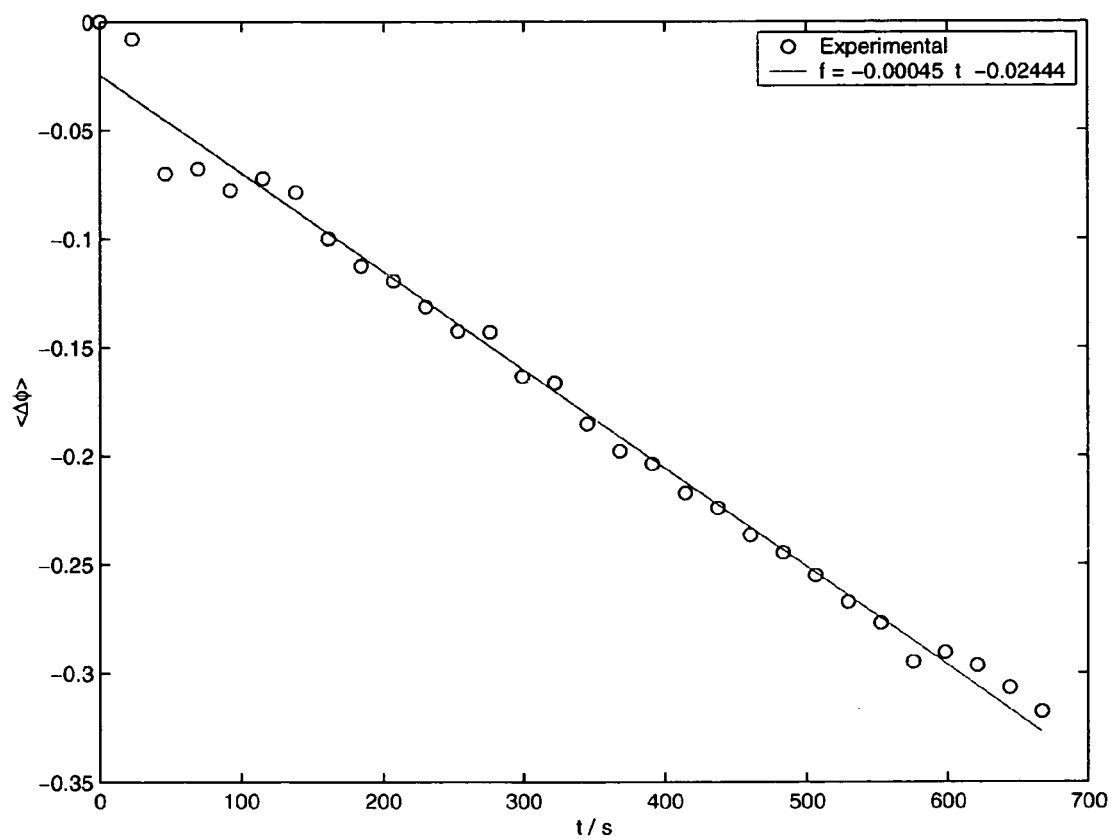
FIG. 4 is a plot of thermally induced nuclear spin phase shift in water measured by a gradient echo sequence versus time following the application of a thermal flux (a laser). From the data the specific heat of water is determined experimentally.

As in FIG. 1A with 11 being air, 12 being a light absorber and 13 being a water sample thermally insulated, a constant thermal power is applied to 12 and the nuclear spin phase shift is measured in an imaging slice by a gradient echo sequence over time. Using P=0.09 W, $R_v=1.9$, $\rho=1$ g/cm³, V=5 cm³ and $d\phi/dt=0.00045$ rads/s from FIG. 4, the specific heat is calculated as C=4.472 J/g·K for a water sample [5].

The specific absorption rate can be measures experimentally through the measurement of specific heat and temperature rate for a substance subjected to electromagnetic radiation.

$$SAR = C\frac{1}{\phi_T}\frac{d\phi}{dt} \quad (25)$$

Once the specific heat is measured it can be used to measure the thermal power of a system by measuring the rate of temperature in a volume of substance. In a constant volume the internal energy change in a substance of mass m is related to the temperature change through the specific heat $$\Delta E = m\cdot C\cdot\Delta T \quad (26)$$

The internal energy change over a time interval then gives the thermal power for a system $$P = \frac{\Delta E}{\Delta t} = \frac{mC}{\omega_T}\frac{\Delta\omega}{\Delta t} \quad (27)$$

in terms of the change in nuclear magnetic resonance frequency.

Figure 5:
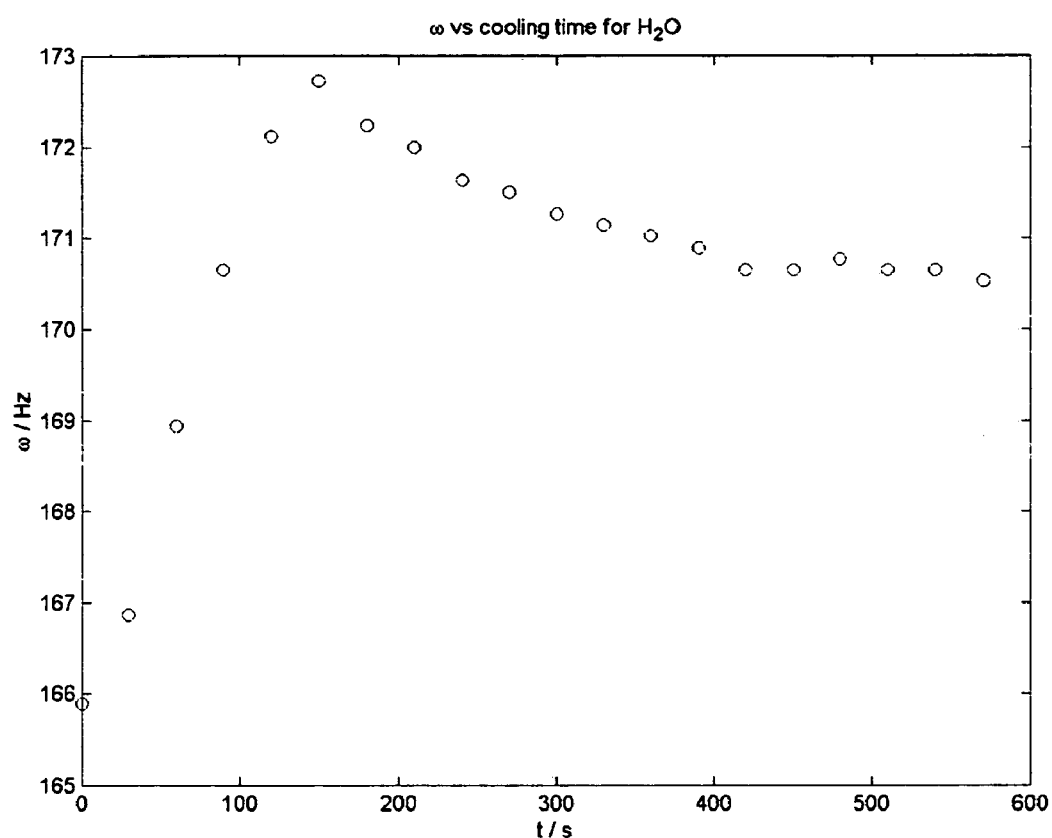
FIG. 5 is a plot of thermally induced nuclear magnetic resonance frequency shift versus time in a water sample subjected to a thermal convection. From the data thermal power of the system is determined experimentally.

Using a water sample of 300 mg, C=4.184 J/g·K, $\omega_T=2.98$ Hz/K and $\Delta\omega/\Delta t=0.06$ Hz/s from FIG. 5, the thermal power can be calculated as P=25.3 mW for thermal convection in the NMR system.

The thermal flux between a body and its environment is proportional to the temperature difference through the heat transfer coefficient. The temperature can be represented as a function of thermally induced nuclear shielding $$T = c_1\sigma + c_2 \quad (28)$$

Then, the thermal energy rate is equal to the internal energy change in terms of nuclear shielding as $$\rho CV\frac{\partial\sigma}{\partial t} = -hS(\sigma - \sigma_\infty) \quad (29)$$

where $\rho$ is density, C is specific heat, V is volume, h is the heat transfer coefficient and S is the surface. Then, the solution of Eq. (29) gives a dimensionless nuclear shielding as $$\theta = \frac{\sigma - \sigma_\infty}{\sigma_0 - \sigma_\infty} = \exp(-t/\tau) \quad (30)$$

where $\sigma_0$ and $\sigma_\infty$ are the nuclear shielding values at the start and at the end of the thermal process, respectively, and $\tau^{-1} = hS/\rho CV$ is the reciprocal thermal decay time. A logarithmic plot of $\theta$ vs. time then gives a curve having a slope of $-\tau^{-1}$ as $$\frac{\partial\ln\theta}{\partial t} = -\frac{1}{\tau} \quad (31)$$

from which the average heat transfer coefficient, h, known as Newton's coefficient, can be calculated [6] as $$h = \tau^{-1} \rho C \frac{V}{S} \qquad (32)$$

The cases of low and high Biot numbers can be examined through any suitable nuclear magnetic resonance parameters to measure the heat transfer coefficients.

The heat transfer coefficient as a function of fluid flow rate is measured using a sample of water, 300 μl, in a 5 mm NMR tube initially brought to a constant temperature, 60° C., and then subjected to convective cooling using a variable rate airflow at room temperature, 24° C., in a $^1$H 300 MHz NMR system (Oxford, SMIS, both of U.K.).

Figure 6A:
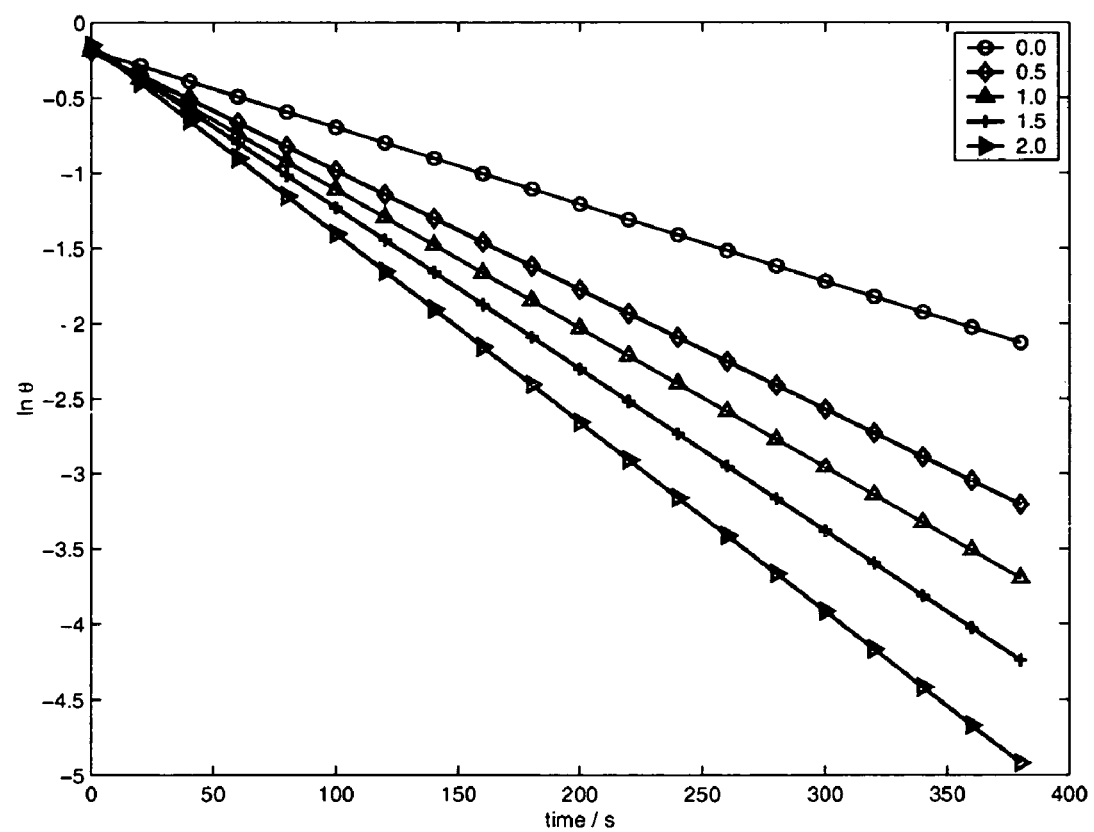
FIG. 6a is a plot of logarithm of dimensionless nuclear shielding versus time for a water sample cooling in air with varying fluid flow rates. From the data the heat transfer coefficient of the substance and fluid system is determined experimentally as a function of fluid flow rate.

A plot of ln θ vs. time for a range of airflow rates is given in FIG. 6a. The slopes of the curves are given by Eq. (31). The experimental heat transfer coefficient as a function of airflow rate, u, is given in Table I.

TABLE I h vs. u for $^1$H 300 MHz NMR

| u (ft$^3$/hr) | 0.0 | 0.5 | 1.0 | 1.5 | 2.0 |
|---|---|---|---|---|---|
| $\tau^{-1}$ (s$^{-1}$) | 0.0043 | 0.0066 | 0.0073 | 0.0086 | 0.0108 |
| h (W/m$^2$·K) | 20.72 | 29.45 | 38.03 | 46.77 | 55.68 |

A linear regression of the experimental data in Table I results in the following relation $$h = k_1 \cdot u + k_2 \qquad (33)$$

where $k_1 = 2.21 \cdot 10^6$ J/m$^5$·K and $k_2 = 20.68$ W/m$^2$·K with air flow rates in m$^3$/s. Here, $k_2$ is the average heat transfer coefficient for natural convection in the NMR. This is a typical literature value for air.

Figure 6B:
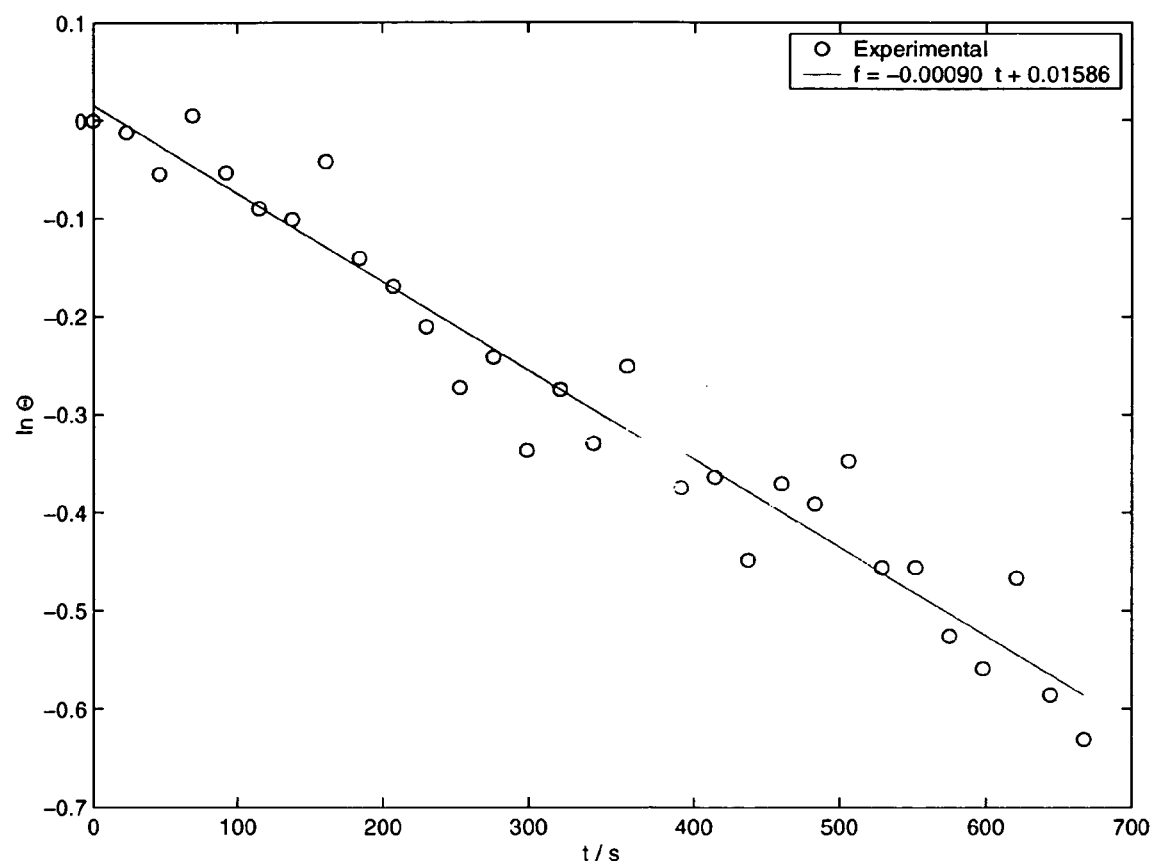
FIG. 6b is a plot of logarithm of dimensionless nuclear magnetization, ln θ, vs. time for a spherical tomato cooling over 2 K by natural convection in a 2 Tesla magnet. From the data the heat transfer coefficient of the substance and fluid is determined experimentally.

A plot of ln θ in terms of dimensionless nuclear magnetization and relaxation ($T_E = 11$ ms) versus time for a spherical tomato cooling over 2K by natural convection (FIG. 1C with 31 being air and 32 being a tomato) in a 2 Tesla magnet (Bruker, Germany) is given in FIG. 6b. Using $\tau^{-1} = 0.0009$ s$^{-1}$ from the experimental data in FIG. 6b, $r_0 = 1.45 \cdot 10^{-2}$ m, $V/S = r_0/3$ and the specific heat and density values of water as C=4185 J/Kg·K and ρ=1000 Kg/m$^3$, respectively for a tomato, the heat transfer coefficient can be calculated as h=18.20 W/m$^2$·K for natural convection in air.

The heat of chemical reactions can be experimentally measured using a nuclear magnetic resonance. As a result of exothermic and endothermic reactions, a chemical reaction in a cell increases or decreases the thermal energy in a substance surrounding the cell. Using a configuration given in FIG. 1, the thermal energy of a known substance such as water can be quantified through an NMR parameter and the heat of reaction can be measured experimentally.

The membrane permeability can be studied by studying the time course of magnetization during the experiment. A number of effects such as volume change, temperature, directional ion flux and ion exchange on the NMR parameters can be measured during the transport processes in various membranes. In the case of a semi-permeable membrane, the magnetization is relative to the number of molecules in the solvent cell whereas in the case of permeable membrane it is relative to both directional flows and concentration effects. These effects can separately be quantified and used in membrane characterization experiments. Using a semi-permeable membrane and an impermeant solute, the directional flux of solvent results in volume change over time from which the apparent membrane permeability coefficient can be measured experimentally. The volume change can be measured by measuring the equilibrium nuclear magnetization.

In the case of a semi-permeable membrane and in the absence of a temperature change, using a very short echo time, the volume as a function of nuclear magnetization and experimental time can be written as $$V(t) = V(0) \frac{M(t_e, t)}{M(t_e, t_0)} \qquad (34)$$

where V(0) is the initial volume of the cell in cm$^3$ and $M(t_e, t_0)$ is the average nuclear magnetization at the start of the experiment, and $M(t_e, t)$ is the average nuclear magnetization at time t during the experiment.

A first order temporal derivative of the volume in Eq. (34) gives the volume flow rate across the membrane as $$J_v \frac{\partial V(t)}{\partial t} = V(0) \frac{\partial}{\partial t} \left[ \frac{M(t_e, t)}{M(t_e, t_0)} \right] \qquad (35)$$

where $J_v$ is the volume flow rate in cm$^3$/s. The permeability coefficient, P, will then be $$P = \frac{J_v}{S} \qquad (36)$$

where P is in cm/s and S is the membrane surface area in cm$^2$. Using the Eqs. (35) and (36), the permeability coefficient of the membrane becomes $$P = \frac{V(0)}{S} \frac{\partial}{\partial t} \left[ \frac{M(t_e, t)}{M(t_e, t_0)} \right] \qquad (37)$$

in terms of initial volume, membrane surface area and the time dependence of nuclear magnetization.

Figure 7:
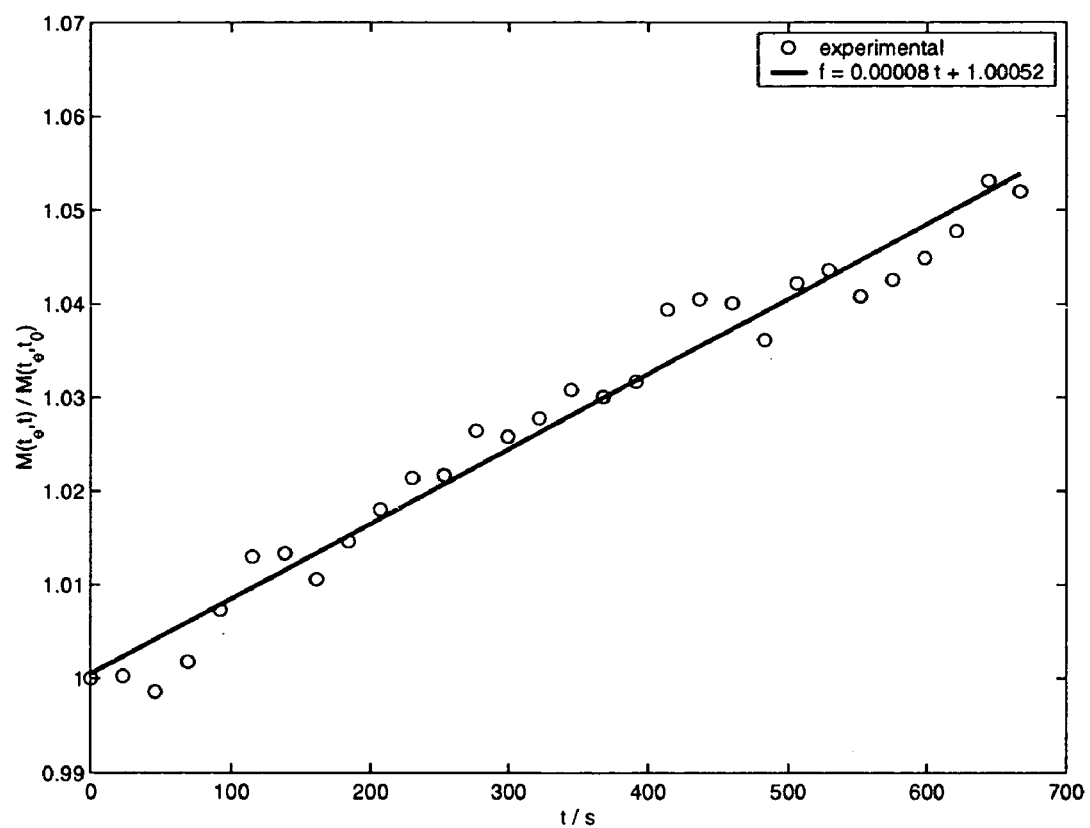
FIG. 7 is a plot of nuclear magnetization and relaxation versus time in a water cell separated by a permeable membrane containing aqueous solution of sodium chloride. From the data apparent permeability coefficient of membrane can be measured experimentally.

As in FIG. 1A with 11 being water, 12 being a permeable membrane and 13 being aqueous solution of sodium chloride, the nuclear magnetization is measured in water by a gradient echo sequence. Using A=0.785 cm$^2$, V(0)=5 cm$^3$ and the slope of 0.00008 s$^{-1}$ from FIG. 7, the apparent membrane permeability coefficient of 5.1 um/s can be estimated for a membrane in a cell containing water and aqueous solution of sodium chloride.

The time dependence of magnetization in the presence of temperature change will include both temperature effects and volume change effects. The measurement of membrane permeability coefficient, P, over a temperature range will allow calculation of Arrhenius activation energy, $E_w$, for the transport through the membrane as $$\frac{\partial \ln P}{\partial (1/T)} = -\frac{E_w}{k_B} \qquad (38)$$

where a plot of ln P versus 1/T from the experimental data gives a slope of $-E_w/k_B$ for the membrane system.

What is claimed is:

1. A method of measuring the thermal diffusivity in a substance by nuclear magnetic resonance, said method comprising:
   a. providing a nuclear magnetic resonance imaging and spectroscopy apparatus,
   b. placing said substance in said nuclear magnetic resonance imaging and spectroscopy apparatus,
   c. measuring one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ or spin—spin relaxation rate $R_2(T)$ or effective spin—spin relaxation time $T_2^*(T)$ or effective spin—spin relaxation rate $R_2^*(T)$ or spin diffusion coefficient $D(T)$ in said substance,
   d. providing a thermal energy to heat a volume in said substance or to heat an absorber placed in close contact with said substance or within said substance,
   e. measuring and normalizing the temporal variation of one or more said nuclear magnetic resonance properties in step (c) in said substance in imaging voxels perpendicular to the direction of the heat propagation at multiple distances from the heated volume or absorber by acquiring multiple nuclear magnetic resonance images,
   f. determining the time for the maximal change in said temporal variation of one or more said nuclear magnetic resonance properties in step (e) at multiple distances,
   g. determining said thermal diffusivity in said substance using the relation between said square of the distance and said time for the maximal change in said temporal variation of one or more said nuclear magnetic resonance properties in step (f).

2. A method of claim 1 wherein said substance is a chemical, a biomedical, a biological, a polymer, a material, a food, a cell, a tissue, a tumor, a human or an animal and said thermal energy is provided by a pulsed or a continuous thermal source.

3. A method of measuring the thermal conductivity in a substance by nuclear magnetic resonance, said method comprising:
   a. placing said substance in a nuclear magnetic resonance imaging and spectroscopy apparatus,
   b. providing a known quantity of a thermal flux to heat a volume in said substance or to heat an absorber placed in close contact with said substance or within said substance,
   c. measuring the temperature dependence of one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ or spin—spin relaxation rate $R_2(T)$ or effective spin—spin relaxation time $T_2^*(T)$ or effective spin—spin relaxation rate $R_2^*(T)$ or spin diffusion coefficient $D(T)$ in said substance,
   d. determining the gradient of one or more said nuclear magnetic resonance properties in step (c) in the direction of the thermal conduction in said substance,
   e. determining said thermal conductivity in said substance using the thermal conduction relation, said thermal flux in step (b), said temperature dependence of one or more said nuclear magnetic resonance properties in step (c), said gradient of one or more said nuclear magnetic resonance properties in step (d).

4. A method of claim 3 wherein said substance is a chemical, a biomedical, a biological, a polymer, a material, a food, a cell, a tissue, a tumor, a human or an animal and said thermal flux is provided by a pulsed or a continuous thermal source.

5. A method of claim 4 wherein said thermal flux is delivered to said substance or said absorber by a laser, and said thermal flux is determined by optically measuring the absorption of said laser in said substance or in said absorber.

6. A method of measuring the specific heat and the specific absorption rate in a substance by nuclear magnetic resonance, said method comprising:
   a. placing said substance in a nuclear magnetic resonance imaging and spectroscopy apparatus,
   b. providing a known thermal power to heat said substance or to heat an absorber placed in close contact with said substance or within said substance,
   c. measuring the temperature dependence of one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ or spin—spin relaxation rate $R_2(T)$ or effective spin—spin relaxation time $T_2^*(T)$ or effective spin—spin relaxation rate $R_2^*(T)$ or spin diffusion coefficient $D(T)$ in said substance,
   d. measuring the temporal variation of one or more said nuclear magnetic resonance properties in step (c) in the heated volume in said substance by acquiring a series of nuclear magnetic resonance images of the heated volume in time,
   e. determining said specific heat in said substance using the thermal power and temperature rise relation, said thermal power, said temperature dependence of one or more nuclear magnetic resonance properties in step (c), said temporal variation of one or more said nuclear magnetic resonance properties in step (d) and the mass of said substance,
   f. subjecting said substance to the electromagnetic radiation and measuring the rate of one or more said nuclear magnetic resonance properties in step (c) in said substance by acquiring a series of nuclear magnetic resonance images of the heated volume in time,
   g. determining said specific absorption rate in said substance using the specific heat and temperature rise relation, said temperature dependence of one or more said nuclear magnetic resonance properties in step (c), said specific heat measured in step (e), said rate of one or more said nuclear magnetic resonance properties measured in step (f).

7. A method of claim 6 wherein said substance is a chemical, a biomedical, a biological, a polymer, a material, a food, a cell, a tissue, a tumor, a human or an animal and said thermal power is provided by a pulsed or a continuous thermal source.

8. A method of claim 7 wherein said thermal power is delivered to said substance or said absorber by a laser, and said thermal power is determined by optically measuring the absorption of said laser in said substance or in said absorber.

9. A method of measuring the thermal power and the thermal energy by nuclear magnetic resonance, said method comprising:
   a. placing the substance in a nuclear magnetic resonance imaging and spectroscopy apparatus,
   b. measuring the temperature dependence of one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ or spin—spin relaxation rate $R_2(T)$ or effective spin—spin relaxation time $T_2^*(T)$ or effective spin—spin relaxation rate $R_2^*(T)$ or spin diffusion coefficient $D(T)$ in said substance,
   c. providing a known thermal power to heat said substance or to heat an absorber placed in close contact with said substance or within said substance, measuring the temporal variation of one or more said nuclear magnetic resonance properties in step (b) in the heated volume in said substance by acquiring a series of nuclear magnetic resonance images of the heated volume in time, determining said specific heat in said substance using the thermal power and temperature rise relation, said thermal power, said temporal variation of one or more said nuclear magnetic resonance properties in step (b), said temperature dependence of one or more nuclear magnetic resonance properties in step (b), and the mass of said substance,
   d. providing a thermal source to heat said substance and measuring the temporal variation of one or more said nuclear magnetic resonance properties in step (b) in the heated volume in said substance by acquiring a series of nuclear magnetic resonance images of the heated volume in time,
   e. determining said thermal power of said thermal source using the thermal power and temperature rise relation, said temperature dependence of one or more said nuclear magnetic resonance properties in step (b), said specific heat of said substance measured in step (c), said temporal variation of one or more said nuclear magnetic resonance properties in step (d) and the mass of said substance,
   f. determining said thermal energy change using said temperature dependence of one or more said nuclear magnetic resonance properties in step (b), said specific heat of said substance measured in step (c), the change in one or more said nuclear magnetic resonance properties in step (d) and the mass of said substance.

10. A method of claim 9 wherein said substance is a chemical, a biomedical, a biological, a polymer, a material, a food, a cell, a tissue, a tumor, a human or an animal and said thermal power is provided by a pulsed or a continuous thermal source.

11. A method of measuring the heat transfer coefficient by nuclear magnetic resonance, said method comprising:
   a. placing the substance in a nuclear magnetic resonance imaging and spectroscopy apparatus,
   b. providing a fluid surrounding said substance and measuring the temporal variation of one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ Or spin—spin relaxation rate $R_2(T)$ or effective spin—spin relaxation time $T_2^*(T)$ or effective spin—spin relaxation rate $R_2^*(T)$ or spin diffusion coefficient $D(T)$ in said substance,
   c. providing a known thermal power to heat said substance or to heat an absorber placed in close contact with said substance or within said substance, measuring the temporal variation of one or more said nuclear magnetic resonance properties in step (b) in the heated volume in said substance by acquiring a series of nuclear magnetic resonance images of the heated volume in time, determining said specific heat in said substance using the thermal power and temperature rise relation, said thermal power, said temporal variation of one or more said nuclear magnetic resonance properties in step (b), said temperature dependence of one or more nuclear magnetic resonance properties in step (b), and the mass of said substance,
   d. determining the thermal relaxation rate by measuring the slope of the logarithm of dimensionless form of one or more said nuclear magnetic resonance properties in step (b) versus time,
   e. determining said heat transfer coefficient using the specific heat and thermal relaxation rate relation, said specific heat measured in step (c), said thermal relaxation rate in step (d), the mass and the surface area of said substance.

12. A method of claim 11 wherein said substance is a chemical, a biomedical, a biological, a polymer, a material, a food, a cell, a tissue, a tumor, a human or an animal and said fluid is at a temperature higher or lower than the temperature of said substance to cause the transport of heat between said substance and said fluid or wherein said fluid is provided with various flow rates.

13. A method of measuring the heat of reaction by nuclear magnetic resonance, said method comprising:
   a. placing at least one substance by itself or imbedded in a surrounding substance in a nuclear magnetic resonance imaging and spectroscopy apparatus,
   b. measuring the temperature dependence of one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ or spin—spin relaxation rate $R_2(T)$ or effective spin—spin relaxation time $T_2^*(T)$ or effective spin—spin relaxation rate $R_2^*(T)$ or spin diffusion coefficient $D(T)$ in said substance or in said surrounding substance,
   c. providing a known thermal power to heat said substance or said surrounding substance or to heat an absorber placed in close contact with said substance or within said substance or with said surrounding substance or within said surrounding substance, measuring the temporal variation of one or more said nuclear magnetic resonance properties in step (b) in the heated volume in said substance or in said surrounding substance by acquiring a series of nuclear magnetic resonance images of the heated volume in time, determining said specific heat in said substance or said surrounding substance using the thermal power and temperature rise relation, said thermal power, said temporal variation of one or more said nuclear magnetic resonance properties in step (b), said temperature dependence of one or more nuclear magnetic resonance properties in step (b), and the mass of said substance or said surrounding substance, d. reacting one or more additional substances in said substance and determining the change in one or more said nuclear magnetic resonance properties in step (b) in said substance or in said surrounding substance, e. determining the thermal energy change as a result of said reaction using said temperature dependence of one or more said nuclear magnetic resonance properties in step (b) in said substance or in said surrounding substance, said specific heat of said substance or said surrounding substance measured in step (c), said change in one or more said nuclear magnetic resonance properties in step (d) in said substance or in said surrounding substance and the mass of said substance or said surrounding substance, f. determining said heat of reaction using the amount of said thermal energy change in said substance or said surrounding substance and the moles of reacting substances, g. determining the reaction to be exothermic on the basis of increase or endothermic on the basis of decrease in said thermal energy change in step (e).

14. A method of claim 13 wherein said substance is a chemical, a biomedical, a biological, a polymer, a material, a food, a cell, a tissue, a tumor, a human or an animal and wherein said reaction is a physical, a chemical, a biomedical or a biological reaction and wherein said reaction is exothermic or endothermic reaction.

15. A method of measuring the membrane permeability by nuclear magnetic resonance, said method comprising:

a. placing one or more substances separated by at least one membrane in a nuclear magnetic resonance imaging and spectroscopy apparatus, b. measuring one or more nuclear magnetic resonance properties comprising nuclear magnetic resonance frequency $\omega$ or nuclear spin phase shift $\phi$ or nuclear magnetization $M(t_e,T)$ or equilibrium nuclear magnetization $M(0,T)$ or spin-lattice relaxation time $T_1(T)$ or spin-lattice relaxation rate $R_1(T)$ or spin—spin relaxation time $T_2(T)$ or spin—spin relaxation rate $R_2(T)$ or effective spin—spin relaxation time $T_2^*(T)$ or effective spin—spin relaxation rate $R_2^*(T)$ or spin diffusion coefficient $D(T)$ in at least one substance on at least one side of at least one membrane, c. measuring the compositional or volume fraction dependence of one or more said nuclear magnetic resonance properties in step (b) in one or more substances on at least one side of at least one said membrane, d. measuring the transport of at least one substance through at least one membrane in time by measuring the temporal variation of one or more said nuclear magnetic resonance properties in step (b) in at least one substance on at least one side of at least one said membrane, e. determining said membrane permeability using the flux relation, said compositional or volume fraction dependence of one or more said nuclear magnetic resonance properties in one or more substances in step (c), said temporal variation of one or more said nuclear magnetic resonance properties in step (d), the initial volume of one or more said substances and the surface area of at least one said membrane.

16. A method of claim 15 wherein said substance is a chemical, a biomedical, a biological, a polymer, a material, a food, a cell, a tissue, a tumor, a human or an animal and wherein said membrane is a chemical or a material or a polymer or a biological membrane or wherein said membrane is a permeable, impermeable or a semi-permeable membrane.

17. A method of claim 15 wherein determining the activation energy of ion transport through said membrane using the exponential relation, the dependence of said membrane permeability on the reciprocal temperature.

18. A method of claim 1 wherein applying at least one of the thermophysical or transport properties for characterization of tissues and tumors in radiology or oncology.

19. A method of claim 18 wherein at least one of said thermophysical or transport properties is different for said tissue and said tumor or at least one of said thermophysical or transport properties is different for said benign tumor and said malignant tumor.

20. A method of claim 6 wherein said temperature dependence of at least one of said nuclear magnetic resonance properties is different for said tissue and said tumor or said temperature dependence of at least one of said nuclear magnetic resonance properties is different for said benign tumor and said malignant tumor.

21. A method of claim 20 wherein characterizing said benign or said malignant tumors on the basis of said temperature dependence of at least one of said nuclear magnetic resonance properties or monitoring the treatment of said tumors on the basis of said temperature dependence of at least one of said nuclear magnetic resonance properties in radiology or oncology.

22. A method of claim 21 wherein said treatment is chemical, radiation or thermal treatment in radiology or oncology.

* * * * *